United States Patent [19]

Rohr

[11] 4,048,217
[45] Sept. 13, 1977

[54] 2-METHYL-3-NITROBENZOIC ACID ESTERS

[75] Inventor: Otto Rohr, Therwil, Switzerland

[73] Assignee: Ciba-Geigy Corporation, Ardsley, N.Y.

[21] Appl. No.: 594,471

[22] Filed: July 9, 1975

[30] Foreign Application Priority Data

July 15, 1974 Switzerland .......................... 9702/74

[51] Int. Cl.$^2$ ............................................. C07C 79/46
[52] U.S. Cl. ......................................... 560/20; 71/88;
71/98; 71/100; 71/105; 71/111; 71/115;
260/347.4; 260/455 R; 260/465 D; 260/502.6;
260/515 R
[58] Field of Search ........................ 260/471 R; 71/111

[56] References Cited

U.S. PATENT DOCUMENTS

3,907,866  9/1975  Theissen .......................... 260/471 R

FOREIGN PATENT DOCUMENTS

2,018,740  6/1970  France
47-41006  10/1972  Japan ...................................... 71/111

OTHER PUBLICATIONS

Haring, Chemical Abstracts, vol. 54 (1960) 13052h.
Erlenmeyer et al., Chemical Abstracts, vol. 42 (1948) 2245g.
Blair et al., Chemical Abstracts, vol. 52 (1958) 10997f.
Hopkinson, J. Chem. Soc. (B) (1969) 203–205.

Primary Examiner—Richard L. Raymond
Attorney, Agent, or Firm—Frederick H. Rabin

[57] ABSTRACT

A composition and method for inhibiting the growth of plants, mono- and dicotyledonous plants such as soya, tobacco cereal grass, ornamental plants are disclosed. The active principle is benzoic acids and esters corresponding to formula

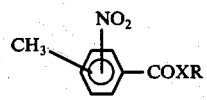

wherein
R is hydrogen, $C_1$–$C_{12}$ alkyl unsubstituted or substituted by halogen, nitro, cyano, $C_1$–$C_4$ alkoxy, $C_1$–$C_4$ alkylcarbonyl, $C_1$–$C_4$ alkylamino, di-$C_1$–$C_4$-alkylamino, $C_3$–$C_6$ cycloalkyl, furyl, tetrahydrofuryl, phenyl that may be substituted by halogen or methyl; $C_2$–$C_{20}$ alkenyl; $C_2$–$C_{20}$ halogenoalkenyl; $C_2$–$C_4$ alkinyl; $C_3$–$C_{20}$ cycloalkyl; phenyl, unsubstituted or substituted by halogen, $C_1$–$C_4$ alkyl; $C_1$–$C_4$ alkoxy; $C_1$–$C_4$ alkylthio; $C_1$–$C_2$ halogenoalkyl, cyano or nitro;
X is oxygen or sulfur.

Some of the esters are disclosed here for the first time.

5 Claims, No Drawings

2-METHYL-3-NITROBENZOIC ACID ESTERS

The present invention relates to a composition for the inhibition of plant growth, to new active substances, to a process for producing these active substances, as well as to the use of these compositions or active substances for the inhibition of plant growth.

The composition according to the invention contains as active substance at least one benzoic acid substituted in the phenyl ring by nitro and methyl, or an ester thereof, corresponding to the formula

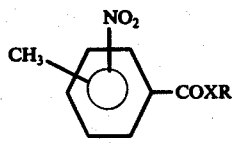

wherein
R represents hydrogen, $C_1$–$C_{12}$-alkyl, unsubstituted or substituted by halogen, nitro, cyano, $C_1$–$C_4$-alkoxy, $C_1$–$C_4$-alkylcarbonyl, $C_1$–$C_4$-alkylamino, di-$C_1$–$C_4$-alkylamino, $C_3$–$C_6$-cycloalkyl, furyl, tetrahydrofuryl, phenyl or phenyl substituted by halogen or methyl, $C_2$–$C_{20}$-alkenyl, $C_2$–$C_{20}$-halogenoalkenyl, $C_2$–$C_4$-alkynyl, $C_3$–$C_{12}$-cycloalkyl, phenyl, unsubstituted or substituted by halogen, $C_1$–$C_4$-alkyl, $C_1$–$C_4$-alkoxy, $C_1$–$C_4$-alkylthio, $C_1$–$C_2$-halogenoalkyl, cyano or nitro, and X represents oxygen or sulphur.

These compounds embrace principally the following groups of benzoic acids and esters thereof:

2-methyl-3-nitrobenzoic acid and the corresponding thio acid thereof, corresponding to the formula

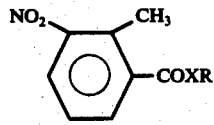

wherein R and X have the above-given meanings;
4-methyl-3-nitrobenzoic acid corresponding to the formula I

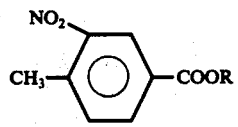

wherein R has the above-given meaning; and
6-methyl-2-nitrobenzoic acid corresponding to the formula

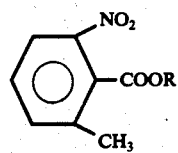

wherein R has the above-given meaning.

The compounds of the formula I and the compositions containing them are excellently suitable for inhibiting the growth of mono- and dicotyledonous plants.

The practical application of the new compositions of the invention or of compounds of formula I for the inhibition of plant growth is new.

The phytotoxicity of N,N-dibutyl-2-methyl-3-nitrobenzoic acid amide has been described by Pagani et al. in "IL FARMACO" 28, (1973) pp. 741–752; the in vitro effect of 2-methyl-3-nitrobenzoic acid on young bean leaves by Lippincott et al., in the Amer. J. Bot. 58, (1971) pp. 817–826.

The methyl-nitrobenzoic acid and its esters of the formula I inhibit the vegetative growth in mono- and dicotyledonous plants, in plant parts both above and below the soil, by imparting to these plants a more compact form. The compounds have only slight toxicity towards warm-blooded animals and, when applied in sensible amounts, produce no harmful effects on the plants. Their action differs from that of a herbicidal active substance or of a fertiliser. The new compositions or their active substances retard vegetative growth, promote formation of blossom, ripening of fruit and development of abscission layers.

The principal field of application for these compositions of the invention is the inhibition of growth in crops of soya beans, tobacco, cereals and grass, and also the inhibition of growth of ornamental plants, bushes (hedges) and also trees.

As a consequence of growth inhibition, it is possible to sow the plants, e.g. soya bean plants, with less space between the rows, a saving in space which renders possible a higher crop yield per unit of surface area. The plants are smaller in size, develop strong green leaves and produce, in proportion to the foilage, a greater blossom and fruit setting. As a result of the plants being closer together, these crops are also better protected against being flattened to the ground by rain and wind.

Due to the inhibition of growth in the case of tobacco plants, there is a reduction in particular in the sprouting of lateral or side shoots, a factor which favours the development of large strong leaves.

In the case of grass, the application of this composition results in a slower rate of growth, so that, e.g., lawns require less frequent cutting; with cereal crops there is formed shorter stronger straw, which has a favourable effect on the formation of the fruit.

The effect of growth inhibition on ornamental plants and ornamental shrubs is that they develop as strong, smaller and uniform plants. Ornamental shrubs require less frequent trimming.

The extent and mode of action depend on the widest variety of factors which vary according to the species of plant; they depend in particular on the applied concentration and on the point of time of application with regard to the development stage of the plant. The active substances are applied preferably in the form of liquid preparations, both to parts of plants above the soil and to or into the soil. The application of the active substances to parts of plants above the soil is the preferred application, for which solutions or aqueous dispersions are most suitable.

The applied amounts have to be adjusted according to the type of cultivated plant and the point of time of application, and are advantageously between 0.01 and 2 kg per hectare.

Many of the methyl-nitrobenzoic acids embraced by the formula I are known: see, e.g., J.Chem.Soc. 1955, pp. 3854–50, J.Am.Chem.Soc. 47, pp. 1395–95 (1927), J.Chromatography 6 p. 396–408 (1961), and J.Am.-Chem.Soc. 67 p. 988–9 (1945), in which publications also esters are in some cases mentioned. Further esters are described, e.g., in J.Chem. Soc. (B) 1969 (3) pp. 203–5, Helv.Chim.Acta 43 p. 104–113 (1961), J.Chem.-Soc. 67, pp. 609–17 (1949), J.Med.Chem. 1968 11 (3), pp. 500–03, or in the U.S. Pat. No. 3,625,989; others are presented here for the first time.

Some compounds embraced by the formula I are new, as well as the esters embraced by the formula Ia

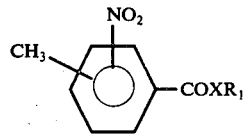
(Ia)

wherein $R_1$ represents a substituted or unsubstituted $C_5$–$C_{12}$-alkyl radical, a $C_3$–$C_{20}$-alkenyl radical or a halogenoalkenyl radical or a $C_2$–$C_4$-alkynyl radical, and X represents oxygen or sulphur.

The substituted alkyl radical $R_1$ can contain the same substituents as are defined for the alkyl radical R under formula I.

Those esters embraced by the formula I of which the production has not yet been described in the literature can be produced by a process wherein a methyl-nitrobenzoic acid of the formula II

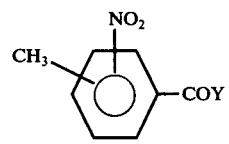
(II), or a reactive derivative thereof, is reacted with an alcohol or thioalcohol, or with the derivative of such an alcohol, of the formula III

R — Z          (III)

under the usual esterification conditions. In the formulae II and III, the symbol R has the meaning given under formula I, while Y and Z represent reactive radicals, and both represent the hydroxyl group, or one of them represents a halogen atom and the other an optionally metallised hydroxyl group or thiol group, e.g. an alkali metal cation or the equivalent of an alkaline-earth metal cation.

It is advantageous to perform the reaction in the presence of a solvent or diluent inert to the reactants. These solvents or diluents are: hydrocarbons such as benzene, toluene or xylenes, halogenated hydrocarbons such as chlorobenzene, methylene chloride, ethylene chloride, chloroform, carbon tetrachloride, N,N-dialkylated amides such as dimethylformamide, also ethers and ethereal compounds such as dialkyl ether, dioxane, tetrahydrofuran or, in the case where Y and Z each represent OH, the corresponding halogenated ethanol. Provided that Y=Z=OH or provided that one of the two symbols represents OH and the other halogen, the process can be performed in the presence of an anhydrous acid or base. Suitable acids are, for example, the following: hydrohalic acids, sulphuric acids, etc., and suitable bases are inorganic bases, such as alkali metal hydroxides and alkaline-earth metal hydroxides or alkali metal oxides or alkaline-earth metal oxides, and organic bases such as tertiary amines.

The esterifications are carried out advantageously under normal pressure at a temperature of between 0° and 100° C.

Preferred embodiments are the esterification of methyl-nitrobenzoic acid and an alcohol of formula III in an inert organic solvent or in an excess of the alcohol of the formula III by means of sulphuric acid; and the reaction of the chloride or bromide of methyl-nitrobenzoic acid with an alcohol or thiol of the formula III in the presence of an inert organic solvent, preferably benzene.

The following Example serves to illustrate the process of the invention. In the subsequent Table there are listed further 2-methyl-3-nitrobenzoic acid esters of the formula I, which have been obtained in a manner analogous to that described in the Example. The temperatures are in degrees Centigrade and the pressures in Torr (1 Torr = 1 mm Hg).

EXAMPLE 1

231 g of 2-methyl-3-nitrobenzoyl chloride is dissolved in 200 ml of benzene, and 205 g of iodoethanol is added. There is subsequently added dropwise at 15°–25°, with cooling and vigorous stirring, 136 g of triethylamine. After completion of the reaction, 100 ml of water is added to the reaction mixtures; the organic phase is separated and is then dried with sodium sulphate. The solvent is filtered off and distilled off. The crystalline residue obtained has the melting point 54°–56° C; yield 372.8 g = 95.6% of theory.

The following esters are produced in analogous manner.

| Compound No. | R | Physical data |
|---|---|---|
| 1 | —CH$_2$CH$_2$I | m.p. 54–56° |
| 2 | —CH$_2$CH$_2$Br | m.p. 43–44° |
| 3 | —CH$_2$CH$_2$Cl | m.p. 50–51° |
| 4 | —CH$_2$CH$_2$CN | m.p. 78–81° |
| 5 | —H | m.p. 182° |
| 6 | —CH$_3$ | m.p. 66–67° |
| 7 | —C$_2$H$_5$ | m.p. 37–38° |
| 8 | —isoC$_3$H$_7$ | m.p. 38–40° |
| 9 | tert. C$_4$H$_9$ | oil $n_D^{25}$ 1,5183 |
| 10 | —CH$_2$—CH=CH$_2$ | oil $n_D^{23}$ 1,5350 |
| 11 | —CH$_2$—C≡CH | m.p. 55–56° |
| 12 | ⟨H⟩ | m.p. 146–150° |
| 13 | ⟨○⟩ | m.p. 81–84° |
| 14 | —C$_2$H$_4$OC$_2$H$_5$ | $n_D^{22}$ 1.5180 |
| 15 | —CH$_2$—⟨○⟩ | $n_D^{22}$ 1.5717 |
| 16 | —CH$_2$—CF$_2$—CHF$_2$ | $n_D^{22}$ 1.4863 |
| 17 | iso C$_5$H$_{11}$ | $n_D^{22}$ 1.5136 |
| 18 | C$_2$H$_4$ (C$_2$H$_5$)$_2$ | $n_D^{22}$ 1.5172 |
| 19 | —CH$_2$—CH(C$_2$H$_5$)—C$_4$H$_9$ | $n_D^{22}$ 1.5020 |
| 20 | nC$_7$H$_{15}$ | $n_D^{22}$ 1.5066 |
| 21 | —CH(C$_2$H$_5$)—C$_4$H$_9$ | $n_D^{22}$ 1.5068 |
| 22 | nC$_{12}$H$_{25}$ | m.p. 44–46° |
| 23 | ⟨○⟩—CH$_3$ | m.p. 73–78° |
| 24 | —CH$_2$—COCH$_3$ | $n_D^{22}$ 1.5392 |
| 25 | n-C$_8$H$_{17}$ | $n_D^{22}$ 1.5053 |

-continued

| No. | R | |
|---|---|---|
| 26 | $(CH_2)_8-\underset{CH_3}{\underset{|}{C}}=CH-C_8H_{17}$ | $n_D^{22}$ 1.5003 |
| 27 | $-CH_2-\underset{CH_3}{\underset{|}{C}}=CH_2$ | $n_D^{22}$ 1.5328 |
| 28 | $-CH_2-CH=CH-CH_3$ | $n_D^{22}$ 1.5300 |
| 29 | $-CH_2-\underset{CH_3}{\overset{CH_3}{\underset{|}{\overset{|}{C}}}}-NO_2$ | m.p. 54–56° |
| 30 | $-CH(CH_2)_{11}$ (cyclododecyl) | m.p. 60–64° |
| 31 | $nC_{10}H_{21}$ | $n_D^{22}$ 1.5021 |
| 32 | $-CH(CH_2Cl)_2$ | $n_D^{22}$ 1.5495 |
| 33 | $-C_6H_4-CF_3$ | m.p. 78–82° |
| 34 | $-C_6H_4-NO_2$ | m.p. 186–187° |
| 35 | $-C_6H_3Cl_2$ | m.p. 124–125° |
| 36 | $-C_6H_4-OCH_3$ | m.p. 77–81° |
| 37 | $-$cyclopentyl | $n_D^{23}$ 1.5360 |
| 38 | $-CH_2-$furyl | $n_D^{22}$ 1.5536 |
| 39 | $-CH_2-$tetrahydrofuryl | $n_D^{22}$ 1.5355 |
| 40 | $-CH_2-C_6H_4-Cl$ | m.p. 90–92° |
| 41 | $-C_2H_4-C_6H_5$ | $n_D^{23}$ 1.5662 |
| 42 | $-\underset{CH_3}{\underset{|}{CH}}-C_6H_5$ | $n_D^{22}$ 1.5647 |
| 43 | $-\underset{CH_3}{\underset{|}{CH}}-$cyclopropyl | $n_D^{23}$ 1.5234 |
| 44 | $-\underset{CH(CH_3)_2}{\underset{|}{CH}}-(CH_2)_5-CH_3$ | $n_D^{22}$ 1.4697 |
| 45 | $-CH[CH_2N(CH_3)_2]_2$ | $n_D^{22}$ 1.5115 |
| 46 | $-\underset{CH_3}{\underset{|}{CH}}-CH_2-C_6H_5$ | $n_D^{22}$ 1.5568 |
| 47 | $-\underset{C_2H_5}{\underset{|}{CH}}-C_6H_5$ | $n_D^{22}$ 1.5550 |
| 48 | $n$-$C_3H_7$ | $n_D^{22}$ 1.5218 |
| 49 | $n$-$C_4H_9$ | $n_D^{22}$ 1.5170 |
| 50 | $n$-$C_5H_{11}$ | $n_D^{22}$ 1.5128 |
| 51 | $n$-$C_6H_{13}$ | $n_D^{22}$ 1.5107 |
| 52 | $n$-$C_9H_{19}$ | $n_D^{22}$ 1.5040 |

$\underset{NO_2\;CH_3}{C_6H_3}-CO-S-R$

| 53 | $nC_{12}H_{25}$ | $n_D^{21}$ 1.5193 |
| 54 | $-CH_2-CH=CH_2$ | $n_D^{21}$ 1.5770 |
| 55 | $-CH_2-C_6H_5$ | m.p. 95–97° |

$\underset{CH_3}{\underset{|}{C_6H_3}}-\underset{NO_2}{\underset{|}{}}-COOR$

| 56 | H | m.p. 187–189° |
| 57 | $isoC_3H_7$ | m.p. 55–58° |

-continued

| 58 | $-CH_2-CH=CH_2$ | $n_D^{22}$ 1.5430 |
| 59 | $-C_2H_4I$ | m.p. 77–80° |
| 60 | $-C_2H_4Cl$ | $n_D^{23}$ 1.5472 |
| 61 | $-C_2H_4Br$ | m.p. 51–54° |
| 62 | $-CH_2-C\equiv CH_3$ | m.p. 58–60° |
| 63 | $nC_8H_{17}$ | $n_D^{23}$ 1.5080 |
| 64 | $-(CH_2)_8CH=CH-C_8H_{17}$ | $n_D^{22}$ 1.4995 |
| 65 | $-CH_2CH=CH-CH_3$ | $n_D^{23}$ 1.5373 |
| 66 | $-CH_2-\underset{CH_3}{\overset{CH_3}{\underset{|}{\overset{|}{C}}}}-NO_2$ | m.p. 87–88° |
| 67 | $-CH(CH_2)_{11}$ | m.p. 81–83° |
| 68 | $nC_{10}H_{21}$ | $n_D^{23}$ 1.5038 |
| 69 | $-CH(CH_2Cl)_2$ | $n_D^{23}$ 1.5510 |
| 70 | $-C_6H_3Cl_2$ | m.p. 143–145° |
| 71 | cyclopentyl | $n_D^{24}$ 1.5388 |
| 72 | $-CH_2-$furyl | $n_D^{23}$ 1.5594 |
| 73 | $CH_2-C_6H_4-Cl$ | m.p. 104–105° |
| 74 | $-\underset{CH_3}{\underset{|}{CH}}-C_6H_5$ | m.p. 81–84° |
| 75 | $-\underset{CH(CH_3)_2}{\underset{|}{CH}}-(CH_2)_5CH_3$ | $n_D^{23}$ 1.4863 |
| 76 | $-CH[CH_2N(CH_3)_2]_2$ | $n_D^{22}$ 1.5167 |
| 77 | $nC_3H_7$ | $n_D^{22}$ 1.5250 |
| 78 | $nC_4H_9$ | $n_D^{22}$ 1.5209 |
| 79 | $nC_5H_{11}$ | $n_D^{22}$ 1.5132 |
| 80 | $nC_6H_{13}$ | $n_D^{22}$ 1.5120 |
| 81 | $nC_9H_{19}$ | $n_D^{22}$ 1.5063 |
| 82 | $-CH_2-CF_2-CF_3$ | $n_D^{24}$ 1.4853 |
| 83 | $-C_2H_4N(C_2H_5)_2$ | $n_D^{24}$ 1.5200 |
| 84 | $-\underset{C_2H_5}{\underset{|}{CH_2CH}}-C_4H_9$ | $n_D^{23}$ 1.5090 |
| 85 | $nC_7H_{15}$ | $n_D^{23}$ 1.5090 |
| 86 | $-\underset{C_2H_5}{\underset{|}{CH}}-C_4H_9$ | $n_D^{23}$ 1.5086 |
| 87 | $nC_{12}H_{25}$ | $n_D^{22}$ 1.5010 |

$\underset{CH_3}{\underset{|}{C_6H_3}}-\underset{NO_2}{\underset{|}{}}-COOR$

| 88 | H | m.p. 151–153° |
| 89 | $-C_2H_4Cl$ | $n_D^{23}$ 1.5434 |
| 90 | $-C_6H_5$ | m.p. 70–74° |
| 91 | $-CH_2-C\equiv CH$ | m.p. 76–78° |
| 92 | $iso\,C_3H_7$ | $n_D^{22}$ 1.5220 |
| 93 | $-CH_2-CH=CH_2$ | $n_D^{23}$ 1.5315 |
| 94 | $-C_2H_4I$ | $n_D^{23}$ 1.5833 |

EXAMPLE 2

Growth Inhibition in Soya Bean Crops

2-Methyl-3-nitrobenzoic acid esters of formula I inhibit the excessive vegetative grown of soya beans and consequently render possible higher crop yields. Comparisons of crop yields were carried out in a field test in the case of various varieties of soya bean.

Plots of about 50 square meters were sprayed in the flowering period with an aqueous preparation of Compound No. 1, and this treatment was repeated 5 times in each test. In addition, a corresponding number of plots were treated with the standard TIBA and left as untreated control plots, respectively. At the same time of harvest, the average height of growth of the plants and the crop yield were determined for each plot. The following results were obtained (average in each case from 5 repeats):

Example 2

| Treatment | Variety Wayne (Nebraska) | | Variety Corsoy (Iowa) | | Variety Lee 68 | |
|---|---|---|---|---|---|---|
| | growth height in inches | yield in bu/acre | growth height in inches | yield in bu/acre | growth height in inches | yield in bu/acre |
| Compound No. 1 0.25 kg/hectare | 31.7 | 46.7 | 28.6 | 39.3 | * | 41.6 |
| TIBA 0.04 kg/hec. | 33.7 | 44.9 | 24.6 | 36.9 | * | 38.4 |
| Control | 34.1 | 45.1 | 30.4 | 35.2 | * | 40.8 |

* = not determined.
TIBA is 2,3,5-triiodobenzoic acid.
An inch (Zoll) = 2.54 cm; an acre (Morgen) = 0.40467 hectares.
A bushel (Scheffel) = 13.892 liters

EXAMPLE 3

Growth Inhibition in Ornamental Plants

Tall-growing chrysanthenums of the varieties "Regal Anne" and "Mme. P Guittet" were grown in pots and, after pinching off, were treated with aqueous preparations of Compound No. 1. A part of the treatment consisted of leaf spraying, the other part of application by watering to the soil in the pots. An evaluation of the growth in height and of the market quality was carried out with fully developed blooms and the results obtained were as follows:

Example 3

| Treatment | Variety Regal Anne | | | Variety Mme. P. Guittet | | |
|---|---|---|---|---|---|---|
| | Growth in height cm | Bloom-quality* | Market-quality* | Growth in height cm | Bloom-quality* | Market-quality* |
| a) Spray treatment | | | | | | |
| 4000 ppm | 20,0 | 1 | 1 | 15,8 | 1 | 2 |
| 2000 ppm | 28,8 | 1 | 1 | 21,0 | 1 | 1 |
| 1000 ppm | 30,4 | 1 | 1 | 22,4 | 1 | 1 |
| b) Watering treatment | | | | | | |
| 500 ppm | 19,2 | 3 | 3 | 14,4 | 3 | 3 |
| 250 ppm | 23,2 | 1 | 1 | 15,8 | 2 | 2 |
| 125 ppm | 26,4 | 1 | 1 | 20,0 | 1 | 1 |
| Control | 44,6 | 1 | 3a) | 33,8 | 1 | 2a) |

*: 1 = good - very good 2 = adequate 3 = inadequate
a) = grown too high as pot plants

EXAMPLE 4

Growth Inhibition in the Case of Grasses (Post-Emergence Method)

Seeds of the grasses *Lolium perenne, Poa pratensis, Festuca ovina* and *Dactylis glomerata* were sown in plastics dishes containing a soil/peat/sand mixture. After 3 weeks, the emerged grasses were cut back to 4 cm above the soil, and 2 days later sprayed with an aqueous spray mixture of the active substance. The amount of active substance was, after conversion, equivalent to 5 kg of active substance per hectare. Fourteen days after application, the growth of the grasses was evaluated according to the following linear scale of values:

Value 1 = severe inhibition (no growth after time of application);

Value 9 = no inhibition (growth as in the case of the untreated control specimen).

There was severe inhibition observed with application of Compounds Nos. 10 and 11, respectively, as active substance.

The compositions according to the invention are produced in a manner known per se by the intimate mixing and/or grinding of active substances of the general formula I with suitable carriers, optionally with the addition of dispersing agents or solvents which are inert to the active substances. The active substances can be obtained and used in the following forms:

solid preparations: dusts, scattering agents, granulates, coated granulates, impregnated granulates and homogeneous granulates;
water-dispersible active-substance concentrates: wettable powders, pastes and emulsions;
liquid preparations: solutions.

The solid preparations (dusts, scattering agents and granulates) are produced by the mixing of the active substances with solid carriers. Suitable carriers are, e.g., kaolin, talcum, bole, loess, chalk, limestone, ground limestone, attapulgite, dolomite, diatomaceous earth, precipitated silicic acid, alkaline-earth silicates, sodium and potassium aluminum silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, dark dust, sawdust, ground nutshells, cellulose powder, residues of plant extractions, active charcoal, etc., alone or in admixture with each other.

The particle size of the carriers is for dusts advantageously up to approx. 0.1 mm; for scattering agents approx. 0.075 to 0.2 mm; and for granulates 0.2 mm or coarser.

The concentration of active substance in the solid preparations is 0.5 to 80%.

It is possible to add to these mixtures also additives stabilising the active substance, and/or nonionic, anion-active and cation-active substances which improve, e.g., the adhesiveness of the active substances on plants and part of plants (adhesives and agglutinants), and/or ensure better wettability (wetting agents) as well a dispersibility (dispersing agents). Suitable adhesives are, for example, olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, lignin-sulphonic acid, the alkali metal salts and alkaline-earth metal salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to obtain any desired concentration. They consist of active substance, carrier, optionally additives stabilising the active substance, surface-active substances, and antifoaming agents and, optionally, solvents. The concentration of active substance in these preparations is 5-80%.

The wettable powders and pastes are obtained by the mixing and grinding of the active substances with dispersing agents and pulverulent carriers, in suitable devices, until homogeneity is obtained. Suitable carriers are, e.g., those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali metal salts, ammonium salts and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary acetylene glycols, dialkyl dilauryl ammonium chloride, and fatty acid alkali-metal and alkaline-earth metal salts.

Suitable anti-foaming agents are, e.g., silicones.

The active substances are so mixed, ground, sieved and strained with the above-mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g., alcohols, benzene, xylenes, toluene, dimethylsulphoxide, N,N-dialkylated amides, N-oxides of amines, especially trialkylamines, and mineral oil fractions boiling in the range of 120° to 350° C. The solvents must be practically odourless, nonphytotoxic, inert to the active substances and not readily combustible.

Furthermore, the agents according to the invention can be used in the form of solutions. For this purpose, the active substance, or several active substances, of the general formula I is dissolved in suitable organic solvents, solvent mixtures, water, or mixtures or organic solvents with water. As organic solvents, it is possible to use aliphatic and aromatic hydrocarbons, their chlorinated derivatives, alkylnaphthalenes, mineral oils in their own or in admixture with each other. The solutions should contain the active substances in a concentration of 1 to 20%.

These solutions can be applied either by means of a propellent gas (as spray), or by means of special sprayers (as aerosol).

Other biocidal active substances or agents can be mixed with the described compositions of the invention. For the broadening of their sphere of action, the new compositions can for example contain, in addition to the stated compounds of the general formula I, insecticides, fungicides, bactericides, fungistatics, bacteriostatics or nematocides. The compositions of the invention may also contain fertilisers, trace elements, etc..

Preparations of the new active substances of the general formula I are described in the following. Parts are given as parts by weight.

Wettable powder

The following constituents are used to produce (a) a 50% wettable powder, (b) a 25% wettable powder, and (c) a 10% wettable powder:

a.
  50 parts of 2-methyl-3-nitrobenzoic acid-(2'-iodoethyl)-ester,
  5 parts of alkylarylsulphonate,
  10 parts of calcium lignin sulphonate,
  1 part of Champagne chalk/hydroxyethylcellulose mixture 1:1,
  20 parts of silicic acid,
  14 parts of kaolin;

b.
  25 parts of 2-methyl-3-nitrobenzoic acid-(2'-iodoethyl ester,
  5 parts of the sodium salt of oleyl methyl tauride,
  2.5 parts of naphthalenesulphonic acid/formaldehye condensate,
  0.5 part of carboxymethylcellulose,
  5 parts of neutral potassium aluminium silicate,
  62 parts of kaolin;

c.
  10 parts of 2-methyl-3-nitrobenzoic acid-(2'-iodoethyl)-ester,
  3 parts of a mixture of the sodium salts of saturated fatty alcohol sulphates,
  5 parts of naphthalenesulphonic acid/formaldehyde condensate,
  82 parts of kaolin.

The active substances are intimately mixed with the additives in suitable mixers and ground in the appropriate mills and rollers. There are obtained wettable powders that can be diluted with water to give suspensions of any desired concentration.

Emulsion concentrate

The following constituents are mixed together to produce a 25% emulsion concentrate:
  25 parts of 2-methyl-3-nitrobenzoic acid-(2'-iodoethyl)-ester,
  5 parts of a mixture of nonylphenolpolyoxyethylene and calcium-dodecylbenzenesulphonate,
  70 parts of xylene.

This concentrate can be diluted with water to obtain emulsions of any desired concentration. Such emulsions are suitable for the accelerated ripening of fruit and for the promotion of the abscission of fruit and leaves.

It is possible to use for producing the wettable powders and the emulsion concentrate, instead of the active substances given, also the other active substances embraced by the formula I.

I claim:

1. 2-Methyl-3-nitrobenzoic acid allyl ester.
2. 2-Methyl-3-nitrobenzoic acid propynyl ester.
3. 2-Methyl-3-nitrobenzoic acid-(2'-iodoethyl)-ester.
4. 2-Methyl-3-nitrobenzoic acid-(2'-chloroethyl)-ester.
5. 2-Methyl-3-nitrobenzoic acid-(2'-bromoethyl)-ester.

* * * * *